US006218492B1

(12) United States Patent
Hill et al.

(10) Patent No.: US 6,218,492 B1
(45) Date of Patent: *Apr. 17, 2001

(54) WATER INSOLUBLE BACTERIOPHOBIC POLYMERS CONTAINING CARBOXYL AND SULFONIC ACID GROUPS

(75) Inventors: Frank Hill, deceased, late of Mettmann, by Hella Luise Hill, heiress by Henning Hinrich Hill, heir; by Friedrich Frank Hill, heir, Waldsee; by Regina Luise Hill, heiress, Speyer; Peter Ottersbach, Windeck, all of (DE); Graciella Djavid, Paris (FR); Marcel Jozefowicz, Lamorlaye (FR); Veronique Migonney, Eaubonne (FR); Jean-Pierre Vairon, Bonzy la Reine (FR)

(73) Assignee: Huels Aktiengesellschaft, Marl (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/065,457

(22) Filed: Apr. 24, 1998

Related U.S. Application Data

(63) Continuation-in-part of application No. 09/001,133, filed on Dec. 30, 1997, now abandoned.

(30) Foreign Application Priority Data

| Jan. 3, 1997 | (DE) | 197 00 076 |
| Jan. 3, 1997 | (DE) | 197 00 077 |
| Jun. 3, 1997 | (DE) | 197 23 132 |
| Jun. 3, 1997 | (DE) | 197 23 131 |

(51) Int. Cl.[7] ............................... C08F 228/02
(52) U.S. Cl. ............................... 526/287; 526/240
(58) Field of Search ............................ 526/287, 240

(56) References Cited

U.S. PATENT DOCUMENTS

| 3,781,248 | * | 12/1973 | Sakai | 526/287 |
| 4,056,517 | * | 11/1977 | Albers | 526/287 |
| 5,756,625 | * | 5/1998 | Crandall | 526/287 |

* cited by examiner

Primary Examiner—Christopher Henderson
(74) Attorney, Agent, or Firm—Oblon, Spivak, McClelland, Maier & Neustadt, P.C.

(57) ABSTRACT

The invention relates to water-insoluble, bacteriophobic and optionally cell proliferation-inhibiting polymers obtainable by free-radical polymerization of (a) at least one monomer of the general formula R—(A)$_a$, in which R is an aliphatically unsaturated organic radical with the valence a, A is a carboxyl group —COOH, sulfuric acid group —OSO$_2$OH, sulfonic acid group —SO$_3$H, phosphoric acid group —OPO(OH)$_2$, phosphonic acid group —PO(OH)$_2$, phosphorous acid group —OP(OH)$_2$, a phenolic hydroxyl group or a salt of one of the groups, and a is 1, 2 or 3, with the proviso that, if the monomer of the formula I contains a carboxyl group —COOH or a carboxylate group, either this monomer contains at least one further radical A having a different one of the definitions specified for A, or at least one further monomer of the formula I is also used in which A has a different one of the definitions specified for A; and (b) at least one other aliphatically unsaturated monomer, wherein the polymers are useful for forming bacteriophobic or cell proliferation-inhibiting articles.

8 Claims, No Drawings

WATER INSOLUBLE BACTERIOPHOBIC POLYMERS CONTAINING CARBOXYL AND SULFONIC ACID GROUPS

This application is a CIP of U.S. Ser. No. 09/001,133 filed Dec. 30, 1997 now abandoned.

BACKGROUND OF THE INVENTION

1. Field of the Invention

The invention relates to water-insoluble polymers useful for preparing bacteriophobic materials and optionally cell proliferation-inhibiting materials, and to processes for the preparation of these polymers. The invention also relates to articles produced using the bacteriophobic materials and optionally cell proliferation-inhibiting materials, and to processes for the preparation of these materials.

2. Description of the Related Art

In all medical examinations, treatments and interventions where articles, instruments or accessories come into direct contact with living tissue and/or body fluids, bacterial contamination can cause considerable difficulties which may even threaten the patient. This applies to short contact just as much to medium-term or long-term applications of implants, catheters, prostheses and other medicotechnical uses. For instance, it is known from P. A. Goldmann, G. B. Pier, Clin. Microbiol. Rev. 6 (1993), 176 ff. that infections in the course of operative interventions may give rise to considerable and costly complications. For the same reasons, catheters need changing after application periods of from 2 to 6 days.

In the field of the food and drink industry, as well, colonization and propagation of bacteria on surfaces of pipelines, containers or packaging are extremely undesirable. In many cases, coats of slime are formed which allow extreme rises in micropopulations, which have a persistent adverse effect on the quality of water, drinks and foods and may even lead to the decay of the product and to damage to the health of the consumers.

Bacteria must be kept away from all fields of life in which hygiene is important. This affects textiles for direct body contact, especially for the genital area and for the care of the elderly and sick. Bacteria must also be kept away from surfaces of furniture and instruments in wards, especially in the area of intensive care and neonatal care, in hospitals, especially in areas for medical interventions, and in isolation wards for critical cases of infection, and also in toilets.

At present, instruments and also surfaces of furniture and textiles are treated against bacteria as required, or else preventatively using chemicals or solutions thereof and using mixtures which, as disinfectants, have a more or less broad and heavy antimicrobial action. Such chemical compositions are nonspecific in their action, are frequently themselves toxic or irritatng, or break down to form products which are objectionable from a health standpoint. In many cases, there are also instances of incompatibility with individuals who are sensitized correspondingly.

A further measure taken against surface bacteria propagation is the incorporation of antimicrobial substances into surface layers, for example the incorporation of silver salts in accordance with WO 92/18098. The incorporation of quaternary ammonium salts into paint-like coatings, moreover, is known from WO 94/13748.

Composites of this kind, however, prove to have little resistance to aqueous solutions or body fluids. Leaching occurs, thereby reducing the concentration of the antimicrobial active substances with the period of application, and lowering the action. Furthermore, when such formulations are used medically, active substance components pass into the physiological circulation, which is extremely undesirable because of toxicological anxieties and potential side-effects.

In a different technical field, U.S. Pat. No. 5,278,200 discloses polymers which comprise carboxylate groups and sulfonate groups in a proportion which is comparable with that of natural heparin. These polymers have anticoagulant properties in relation to thrombocytes in the blood.

Furthermore, diverse attempts are made to immobilize antimicrobial substances on polymeric and/or functionalized surfaces, preferably by means of covalent bonds (T. Ouchi, Y. Ohya, Prog. Polym. Sci., 20 (1995), 211 ff.). In this case chemical bonding to a substrate leads to a reduction in the bactericidal action in comparison with the free active substances. In the case of medical applications, surfaces of this kind often display instances of incompatibility with the physiological system.

In addition, the bacteria which have been killed remain on antimicrobial surfaces and build up organic layers which, ultimately, completely mask the bactericidal actions. The covering of the surface with dead bacteria constitutes a particularly advantageous nutrient base for further microbial infestation (A. Kanazawa, T. Ikeda, T. Endo, J. Polym. Sci. A. Polym. Chem., 31 (1993),1467 ff.).

In the case of certain medical uses, it is not only the bacteriophobic properties of the plastics used that are important but also cell proliferation-inhibiting properties. For example, cell colonization in the case of catheters applied intracorporally in the medium term (indwelling catheters) is just as harmful as in the case of cardiac valves or stents which are implanted for a long period. WO 94/16648 describes a process in which cell sorption and cell propagation on eye implant lenses, which cause clouding of the lens, are prevented by subsequent chemical modification of the surface of the implant. In accordance with EP 0 431 213, polymers are equipped with cell-repelling properties by rendering the surfaces of the polymers hydrophilic using strong mineral acids. This leads to a reduction in cell adhesion.

The subsequent chemical modification of surfaces of polymeric materials is in most cases irregular and/or non-uniform. Untreated areas remain in many cases, and may form starting points for cell colonization of the surface.

The present invention, then, is based on the object of providing a process by which surfaces of polymers can be kept substantially free from bacteria and, optionally at the same time, free from cell colonization in a physiologically compatible manner and without the bacteria which have been killed remaining on the surface. A further object is to provide bacteriophobic and optionally at the same time cell proliferation-inhibiting polymers. Another object of the invention is to provide articles which consist of or comprise certain bacteriophobic and optionally at the same time cell proliferation-inhibiting materials.

SUMMARY OF THE INVENTION

One of the subjects of the present invention is a process for preparing bacteriophobic and optionally cell proliferation-inhibiting polymer surfaces, which comprises using water-insoluble polymers A which are obtainable by free-radical polymerization of (a) at least one monomer of the general formula $$R—(A)_a \qquad \text{Formula I}$$

in which
R is an aliphatically unsaturated organic radical with the valence a,
A is a carboxyl group —COOH, sulfuric acid group —$OSO_2OH$, sulfonic acid group —$SO_3H$, phosphoric acid group —$OPO(OH)_2$, phosphonic acid group —$PO(OH)_2$, phosphorous acid group —$OP(OH)_2$, a phenolic hydroxyl group or a salt of one of the groups, and
a is 1, 2 or 3;
with the proviso that, if the monomer of the formula I contains a carboxyl group or a carboxylate group, either this monomer contains at least one further radical A having a different one of the definitions specified for A, or at least one further monomer of the formula I is also used in which A has a different one of the definitions specified for A; and
(b) at least one other aliphatically unsaturated monomer.

The invention is based on the observation that the polymers A are highly suitable for use as bacteriophobic and optionally cell proliferation-inhibiting materials, in bulk or for coating.

The term aliphatically unsaturated radical R as used here and below is intended to denote an organic radical comprising C—C double and/or triple bonds, preferably one or two olefinic double bonds. The organic radical R can have a hydrocarbon structure or may contain further atoms in addition to carbon and hydrogen, for example oxygen, nitrogen and/or silicon atoms.

The above restrictive proviso condition excludes the less effective copolymers which contain only one carboxyl or carboxylate group.

Among the salts of the acidic groups specified for A, preference is given to the alkali metal salts and in particular to the sodium salts.

The common feature of the monomers of the formula I is that they have preferably 1 or 2 olefinic double bonds and also at least one acidic group or a salt of an acidic group, it being not possible, as mentioned above, for the carboxyl and the carboxylate group to occur alone.

The polymers A which are to be used in accordance with the invention are barely infested by bacteria. Consequently, the adhesion of bacteria on the surface is outstandingly suppressed. In addition to this bacteriophobic action, the polymers to be used in accordance with the invention are also bacteriostatic; in other words, the cell division of the few bacteria which have adhered to the surface of the polymers is greatly reduced. This means that the bacteriophobic action of the polymers according to the invention cannot be masked by the growth of bacteria which have already adhered. The reduction in the adsorption and multiplication of bacteria relates, for example, to the following types of Gram-positive and Gram-negative strains: *Staphylococcus epidermidis, Streptococcus pyogenes, Staphylococcus aureus, Klebsiella pneumoniae, Pseudomonas aeruginosa, Escherichia coli* and *Enterobacter faecium*.

The particular conditions in which a polymer A is bacteriophobic and at the same time inhibits cell proliferation will be explained later.

The surfaces of the polymers A are not only bacteriophobic and optionally cell proliferation-inhibiting but in addition are outstandingly compatible with tissue, blood or other body fluids, since antimicrobial active substances are not employed and thus are also unable to enter the body.

Another subject of the invention are water-insoluble, bacteriophobic and optionally cell proliferation inhibiting polymers B, obtainable by free-radical copolymerization of
(a) one or more aliphatically unsaturated monomers which contain carboxyl groups and/or carboxylate groups, or the correspondingly functionalized derivatives of these monomers, as component I, with
(b) one or more aliphatically unsaturated monomers containing sulfonic acid groups and/or sulfonate groups, or the correspondingly functionalized derivatives of these monomers, as component II, and
(c) a component III which comprises a further aliphatically unsaturated monomer or a plurality of further aliphatically unsaturated monomers, the correspondingly functionalized derivatives being converted if desired, after copolymerization and at least on the surface, into carboxyl or carboxylate groups or sulfonic acid or sulfonate groups, respectively.

A further subject of the present invention is a process for preparing the water-insoluble, bacteriophobic polymers B, which comprises subjecting
(a) one or more aliphatically unsaturated monomers which contain carboxyl groups and/or carboxylate groups, or correspondingly functionalized derivatives of these monomers, as component I, to free-radical copolymerization with
(b) one or more aliphatically unsaturated monomers containing sulfonic acid groups and/or sulfonate groups, or correspondingly functionalized derivatives of these monomers, as component II, and
(c) a component III which comprises a further aliphatically unsaturated monomer or a plurality of further aliphatically unsaturated monomers, the correspondingly functionalized derivatives being converted if desired, after copolymerization and at least on the surface, into carboxyl or carboxylate groups or sulfonic acid or sulfonate groups, respectively.

The novel copolymers B are a subgroup of the above-described polymers A which are used to prepare bacteriophobic surfaces. The statements regarding the properties for polymers A therefore also apply to the polymers B. Functionalized derivatives of the groups are, in particular, ester, amide and nitrile groups. They are optionally converted subsequently, at least on the surface (and it is only this which is important for the bacteriophobic and bacteriostatic and also the cell proliferation-inhibiting action) into carboxyl or carboxylate groups or sulfonic acid or sulfonate groups, respectively, for example by means of acidic or basic hydrolysis.

Preferred polymers B contain carboxylate and sulfonate groups. In so far as these groups are not introduced by the choice of appropriate monomers, they can be generated subsequently, at least on the surface, by neutralizing carboxyl groups or sulfonic acid groups with the solution of a base, such as sodium hydroxide solution, or by basic hydrolysis of ester groups.

For the polymers B according to the invention it is also possible to employ an aliphatically unsaturated monomer which contains both carboxyl and/or carboxylate groups and sulfonic acid and/or sulfonate groups. Bifunctional monomers of this kind function simultaneously as components I and II.

Alternatively, aliphatically unsaturated monomers each containing two or more carboxyl and/or carboxylate groups or sulfonic acid and/or sulfonate groups, or correspondingly functionalized derivatives of these monomers can be used.

For the polymers B according to the invention, the sum of the proportions of component I and of component II is judiciously from 0.5 to 30 mol % of the polymer.

The ratio of the carboxyl and/or carboxylate groups present in the polymer B according to the invention to sulfonic acid and/or sulfonate groups is advantageously from 0.5 to 10, preferably from 0.5 to 5. If the ratio is from 0.4 to 3, preferably from 0.4 to 2, the polymers B also exhibit pronounced cell proliferation-inhibiting properties.

DESCRIPTION OF THE PREFERRED EMBODIMENTS

Monomers of the polymers A and B

Suitable examples of components I and II for the preparation of the polymers B according to the invention are monomers of the general formulae II and III, $$(C_nH_{2n-q-2})(COOR^1)_x \text{ (for component I)} \quad \text{Formula II}$$

$$(C_nH_{2n-q-x})(SO_3R^1)_x \text{ (for component II)} \quad \text{Formula III}$$

which come under the formula I and are preferred monomers for the preparation of polymers B. In the formulae II and III n independently at each occurrence is an integer from 2 up to and including 6, q independently at each occurrence is 0 or 2, x independently at each occurrence is 1 or 2; and the radical $R^1$, independently at each occurrence, is —H, an equivalent of a metal ion, especially an alkali metal ion, or a radical of an aliphatic, cycloaliphatic or araliphatic alcohol, preferably of an alkanol having 1 to 6, especially 1 to 4 carbon atoms, of a cycloalkanol having 5 to 12 carbon atoms, of an arylalkanol having 7 to 10 carbon atoms, or of an alkanol having oxygen and/or nitrogen atoms in the chain and up to 12 carbon atoms.

Where the groups $(COOR^1)_x$, and $(SO_3R^1)_x$ are ester groups, they are converted after polymerization, by hydrolysis, into carboxyl or carboxylate groups or sulfonic acid or sulfonate groups, respectively.

In accordance with the definitions given the radical $(C_nH_{2n-q-x})$ independently at each occurrence is a straight-chain or branched monovalent alkenyl radical (q=0, x=1) or alkadienyl radical (q=2, x=1) or a straight-chain or branched divalent alkenylene radical (q=0, x=2) or alkadienylene radical (q=2, x=2).

Instead of two monomers of the formulae II and II it is also possible in turn to employ only one bifunctional monomer (II+III), which comprises the groups $COOR^1$ and $SO_3R^1$ in the same molecule.

As a special case of monomers suitable as component I mention may be made of the following monomers of the formula IV which come under the formula II:

$$(C_nH_{2n-q-x})(COOR^2)_x, \quad \text{Formula IV}$$

where $R^2$=—(CH$_2$—CH$_2$—O)$_d$—H, —(CH$_2$—CH(CH$_3$)—O)$_d$—H, —(CH$_2$—CH$_2$—CH$_2$—O)$_d$—H or —(CH$_2$)$_d$—NH$_{2-e}$(R$^3$)$_e$, where R$^3$ is —CH$_3$ or —C$_2$H$_5$, d is 0, 1, 2, 3 or 4 and e is 0, 1 or 2, n is 2, 3, 4, 5 or 6, q is 0 or 2, and x is 1 or 2.

Following polymerization, the carboxylic ester groups are hydrolyzed and are then in the form of carboxyl or carboxylate groups. The aliphatically unsaturated monomers can be either straight-chain or branched.

As a special case of monomers which are suitable as component II mention may be made of the following monomers of the general formula V, which fall under the formula III:

$$(C_nH_{2n-q-x})(SO_3R^2)_x, \quad \text{Formula V}$$

in which, $R^2$, n, q and x are as defined.

The sulfonic ester groups are hydrolyzed after polymerization and are then in the form of sulfonic acid groups or sulfonate groups. The aliphatically unsaturated monomers can be either straight-chain or branched.

In addition, benzene-derived monomer components of the general formula VI $$(C_6H_{6-a-b-c})A_aB_b(OH)_c \quad \text{Formula VI}$$

are suitable as components I and II for the polymer B, where

A independently at each occurrence is a mono- or divalent straight-chain or branched radical of the formula —(C$_n$H$_{2n-1-q-y}$)(COOR$^1$)$_y$ or —(C$_n$H$_{2n-1q-y}$)(SO$_3$R$^1$)$_y$ in which R$^1$, n, and q, are as defined above, and y is 0, 1 or 2;

B independently at each occurrence is C$_{1-4}$-alkyl, —NH$_2$, —COOH, —SO$_3$H, —OSO$_3$H, —OPO(OH)$_2$, —PO(OH)$_2$, —OP(OH)$_2$, —PO(O$^-$)OCH$_2$CH$_2$N$^+$(CH$_3$)$_3$, —PO(O$^-$)OCH$_2$—CH$_2$N$^+$(CH$_3$)$_3$, —OP(O$^-$)OCH$_2$CH$_2$N$^+$(CH$_3$)$_3$ or is optionally a salt, especially an alkali metal salt, or an ester of the groups;

a is 1, 2, or 3;

b is 0, 1, 2 or 3; and c is 0, 1, 2, or 3;

with the proviso that a+b+c≦6, advantageously ≦4.

Depending on the definition of A, the monomers of the formula VI are suitable as component I or as component II.

As a special case of monomers which fall under the general formula VI and which are suitable as component I mention may be made of the following monomers of the general formula VII.

$$(C_6H_{6-a-b-c})C_aD_b(OH)_c, \quad \text{Formula VII}$$

in which

C=(C$_n$H$_{2n-q-y-1}$)(COOR$^2$)$_y$, where

R$^2$=—(CH$_2$—CH$_2$—O)$_d$—H, —(CH$_2$—CH(CH$_3$)—O)$_d$—H, —(CH$_2$—CH$_2$—CH$_2$—O)$_d$—H or —(CH$_2$)$_d$—NH$_{2-e}$(R$^3$)$_e$, where R$^3$ is —CH$_3$ or —C$_2$H$_5$, d is 0, 1, 2, 3 or 4 and e is 0, 1 or 2, n is 2, 3, 4, 5 or 6, q is 0 or 2, and y is 0, 1 or 2;

D=—COOH, —SO$_3$H, —NH$_2$, —N$^+$(CH$_3$)$_3$, —O—PO$_3$H, OSO$_3$H, or —O—PO$_2^-$—CH$_2$—CH$_2^-$N$^+$(CH$_3$)$_3$, a is 1, 2 or 3, b is 0, 1, 2 or 3, and c is 0, 1, 2 or 3;

with the proviso that a+b+c≦6, advantageously ≦4

As a special case of monomers which fall under the general formula VI and which are suitable as component II mention may be made of the following monomers of the general formula VIII:

$$(C_6H_{6-a-b-c})E_aD_b(OH)_c, \quad \text{Formula VIII}$$

in which

E=(C$_n$H$_{2n-q-y-1}$)(SO$_3$R$^2$)$_y$, where

R$^2$=—(CH$_2$—CH$_2$—O)$_d$—H, —(CH$_2$—CH(CH$_3$)—O)$_d$—H, —(CH$_2$—CH$_2$—CH$_2$—O)$_d$—H or —(CH$_2$)$_d$—NH$_{2-e}$(R$^3$)$_e$, where R$^3$ is —CH$_3$ or —C$_2$H$_5$, n is 2, 3, 4, 5 or 6, q is 0 or 2,
y is 0, 1 or 2,
d is 0, 1, 2, 3 or 4 and
e is 0, 1 or 2;
D=—COOH, —SO$_3$H, —NH$_2$, —N$^+$(CH$_3$)$_3$, —O—PO$_3$H, —OSO$_3$H, or —O—PO$_2^-$—CH$_2$—CH$_2$—N$^+$(CH$_3$)$_3$,
a is 1, 2 or 3,
b is 0, 1, 2 or 3, and
c is 0, 1, 2 or 3;
with the proviso that a+b+c≦6, advantageously ≦4.

In the two latter special cases as well, esters groups are hydrolyzed after polymerization and are then in the form of the corresponding acidic or ionic neutralized groups.

Of the monomers of the general formulae I to VIII which are suitable for preparing the coating polymers and which contain one or more identical or different actual or potential (i.e. actual after-hydrolysis) radicals A in the molecule, mention may be made by way of example of acrylic acid, sodium acrylate, isobutyl acrylate, 2-ethylhexyl acrylate, 2-hydroxyethyl acrylate, 2-(2'-hydroxyethoxy)ethyl acrylate, 2-hydroxy-1-methylethyl acrylate, 2-N,N-dimethylaminoethyl acrylate, methacrylate, sodium methacrylate, n-propyl methacrylate, 2-hydroxyethyl methacrylate, 2-(2'-hydroxyethoxy)ethyl methacrylate, 2-hydroxy-1-methylethyl methacrylate, 2-N,N-dimethylaminoethyl methacrylate, maleic acid, diethylene glycol methacrylate, triethylene glycol diacrylate, sodium allyl sulfate, sodium methallyl sulfate, 2-hydroxyethyl allyl sulfate, vinylsulfonic acid, sodium vinylsulfonate, 2-hydroxyethyl vinylsulfonate, vinylbenzenesulfonic acid, sodium vinyltolylsulfonate, 4-vinylsalicylic acid, 1,3-butadiene-1,4-diol diphosphate, sorbic acid, caffeic acid, 4- and 2-vinylphenol, 2-allylhydroquinone, 4-vinylresorcinol and carboxylstyrenesulfonic acid.

Further monomers

Further aliphatically unsaturated monomers (b), in connection with the polymer B also referred to as component III, which are suitable for the polymers B and for the abovementioned polymers A are, preferably, monomers which carry no ionic groups. The aliphatically unsaturated monomers (b) make a predominant contribution to the insolubility of the polymers A and B in water. By means of guideline experiments it is easy to determine which monomers in what amount can be employed as monomers (b) in order that the polymers A and B are insoluble in water. They are regarded as being insoluble in water when they undergo no visible change even after a period of months in contact with aqueous media in the course of the use as intended of the articles produced from them or of the articles coated with them. Examples of the monomers which are suitable in principle as aliphatically unsaturated monomers (b) include vinyl compounds, for example vinyl ketones, such as vinyl ethyl ketone and vinyl n-butyl ketone, vinyl esters, such as vinyl acetate and vinyl propionate; allyl compounds; (meth) acrylic compounds, such as (meth)acrylic esters, for example methyl acrylate, methyl methacrylate, n-butyl acrylate and 2-ethylhexyl acrylate, and also acrylonitrile and acrylamide; olefins and dienes, such as 1-butene, 1-hexene, 1,3-butadiene, isoprene and chloroprene, unsaturated halogenated hydrocarbons, such as vinyl chloride and vinylidene chloride; vinylsiloxanes, such as tris(trimethylsiloxy) methacryloylsilane and tris(trimethylsiloxy) acryloylpropylsilane; and the correspondingly functionalized derivatives thereof. If, and in so far as, carboxylic ester groups, nitrile groups and carboxamide groups are not subsequently hydrolyzed, the corresponding monomers are also valid as aliphatically unsaturated monomers (b).

Preparation of the bacteriophobic and optionally cell proliferation inhibiting polymers A and B The polymers A and B according to the invention or to be used in accordance with the invention can be prepared, for example, by means of emulsion polymerization in accordance with the prior art (Hans-Georg Elias, Makromoleküle, Hüthig & Wepf Verlag, Heidelberg, 1981, p. 603 ff.).

Furthermore, to prepare the polymers B according to the invention, the components I, II and III can also be copolymerized in solution or in bulk by known methods (Hans-Georg Elias, Makromoleküle, Hüthig & Wepf Verlag, Heidelberg, 1981, p. 602 ff.)

For copolymerizing the components I, II and III in solution it is possible to employ, for example, the following solvents (depending on the monomers employed): water, ketones, such as acetone, methyl ethyl ketone, butanone and cyclohexanone, ethers, such as diethyl ether, tetrahydrofuran and dioxane- alcohols, such as methanol, ethanol, n- and isopropanol, n- and isobutanol and cyclohexanol; strongly polar solvents, such as dimethylacetamide, dimethyl sulfoxide and dimethylformamide; hydrocarbons, such as heptane, cyclohexane, benzene and toluene; halogenated hydrocarbons, such as dichloromethane and trichloromethane; esters, such as ethyl acetate, propyl acetate and amyl acetate; and also nitrites, such as acetonitrile.

Polymerization initiators which can be used include azo nitrites, alkyl peroxides, acyl peroxides, hydroperoxides, peroxo ketones, peresters and peroxocarbonates, peroxodisulfate, persulfate and all customary photoinitiators. Polymerization can be initiated thermally or by means of electromagnetic radiation, such as UV light or gamma radiation.

If the monomers employed to prepare the bacteriophobic and optionally cell proliferation-inhibiting polymers comprising monomers of the formulae II to VIII are not monomers which contain carboxyl and/or carboxylate groups or sulfonic acid and/or sulfonate groups, but the functionalized derivatives thereof, for example a carboxylic ester instead of a carboxylic acid, then following polymerization the functionalized derivatives must be converted into carboxyl or carboxylate groups and/or sulfonic acid or sulfonate groups, respectively. In the case of the esters this can be done by means of acid- or base-catalyzed hydrolysis. Polymeric materials can be derivatized by generally known methods (Hans Beyer, Lehrbuch der organischen Chemie, S. Hirzel Verlag, Stuttgart, 1988, p. 260 ff.).

Use of the polymers

A further subject of the present invention is the use of the water-insoluble polymers A and B for producing articles having a bacteriophobic and optionally cell proliferation-inhibiting surface. These include articles consisting wholly or in part of these polymers and articles made from plastic, ceramic or metal which are coated with the polymers. Suitable coating techniques are the known techniques such as dipping, spraying, brushing, knife coating and spin coating. Coating with the polymers according to the invention makes it possible to continue to use known and well-established materials and production methods. This is particularly advantageous when the mechanical properties of the materials are important or when high levels of capital investment were required for the existing production plants in accordance with the production methods to date.

It is also possible to fix the polymers by means of primer layers or intermediate layers comprising bifunctional compounds on standard polymers, which may have been activated. Examples of such standard polymers are PVC, polystyrene, polyurethanes, polyacrylates, polymethacrylates, polyesters, polyethers, polyether-block-amides, polyamides, polycarbonates, polyolefins, silicones and polytetrafluoroethylene.

The articles produced in accordance with the invention with a bacteriophobic and optionally cell proliferation-inhibiting surface are intended preferably for use in the fields of food and tobacco technology, water engineering, biotechnology, preventive hygiene and, in particular, medical engineering. For example, the polymers described here can be used to produce articles such as textiles, furniture and instruments, tubes and hoses, flooring, wall and ceiling surfaces, storage containers, packaging, window frames, telephone receivers, toilet seats, door handles, grips and holding straps in public transport, and medical articles which consist of the polymers or have a coating of these polymers on plastics, ceramics or metal as the substrate. Examples of medical articles are implants or accessories, such as drainage tubes, leads, cannulas, intraocular lenses, contact lenses, stents, vascular prostheses, artificial limbs, bone substitute materials, artificial ligaments, dental prostheses for plastic surgery, blood bags, dialysis membranes, suture materials, dressings, nonwoven products and surgical instruments. A preferred use of the materials according to the invention is for producing catheters.

Articles according to the invention

A final subject of the present invention are the articles, which have been prepared using the water-insoluble, bacteriophobic and optionally cell proliferation-inhibiting polymers, as has been described above, especially the abovementioned medical articles, and preferably catheters.

The examples which follow are intended to illustrate the invention in more detail but without restricting its scope as defined in the patent claims.

EXAMPLES

Test Methods For Bacterial Adhesion

Measuring bacterial adhesion by scintillation

The samples of the respective polymers according to the invention, obtained by copolymerization, are dissolved in an appropriate solvent. The solutions are poured into a Petri dish and the solvent is evaporated, and the resulting polymer films are immersed for a period of one hour in 1 ml of a solution consisting of phosphate-buffered saline (PBS), 0.4 g/l bovine serum albumin (BSA) and 20 μg/ml purified human fibronectin. The samples thus coated with fibronectin are then placed with vigorous stirring for 1 hour at 37° C. into the corresponding bacterial suspension, which has been radiolabeled by the incorporation of 3H-thymidine. After the predetermined time has elapsed the excess bacteria are removed and the membranes are rinsed 3 times with in each case 3 ml of a PBS-BSA solution and are placed in a sample chamber with 20 ml of scintillation solution in order to determine the number of bacteria which have adhered. The percentage of adhered bacteria is determined from the ratio of the radioactivity originating from the sample to the amount of radioactivity originally introduced by the bacteria. The reference sample used is a film prepared in the same way which is obtained by polymerization of component III of the respective polymer according to the invention. The inhibition of bacterial adhesion is expressed as a percentage quotient of the bacterial adhesion of the reference film to that of the polymer according to the invention.

Measuring the bacterial adhesion of coated standard films using ATP (static)

Following the adsorption of microbe cells on films of the respective polymer according to the invention, the bacteria which have not adhered are rinsed off using sterile PBS buffer solution. The adenosine triphosphate (ATP), a substance present in bacteria, is extracted from the bacteria which have adhered to the film and is measured using a customary commercial test combination in a bioluminometric assay. The number of light pulses measured is proportional to the number of bacteria which are adhering. Since the ATP content of the different bacterial strains is different, a plurality of standard films are employed in each case. The reference sample used is a film prepared in the same way which is obtained by polymerizing component III of the respective polymer according to the invention. The inhibition of bacterial adhesion is expressed as a percentage quotient of the bacterial adhesion of the reference film to that of the polymer according to the invention.

Measuring the bacterial adhesion of coated standard films using ATP (dynamic)

The bacteria are placed, together with the film of the respective polymer according to the invention that is to be tested, in a yeast extract/peptone/glucose nutrient solution, and the mixture is shaken at 37° C. for 24 hours. Subsequently, the section of plastic is rinsed with tap water, transferred to a fresh flask containing nutrient solution and shaken for a further 24 hours at 37° C. After that, the latter procedure is repeated once, and the section of film is rinsed with tap water and immersed in sterile PBS. The adenosine triphosphate (ATP), a substance present in cells, is extracted from the bacteria which are adhering to the film and is measured using a customary commercial test combination in a bioluminometric assay. This value is proportional to the bacteria which have adhered. The reference sample used is a film prepared in the same way which is obtained by polymerizing component III of the respective polymer according to the invention. The inhibition of bacterial adhesion is expressed as a percentage quotient of the bacterial adhesion of the reference film to that of the polymer according to the invention.

The results set out in the following examples show that the adhesion of bacteria to polymers according to the invention, irrespective of the strain of bacteria and the measurement method, is from 95 to 99%, i.e. virtually complete. This action is also not masked by dead microorganisms.

Method of Determining the Cell Proliferation

Preparing the cell suspension

Human fibroblasts (McCoy's) from ATCC No. CRL 1696 (Rockville, Md., USA) are grown in DMEM (Dulbecco's Modified Eagles Medium) with the addition of antibiotics, L-glutamine and 10% by volume of fetal calf serum at 37° C. under an atmosphere of 5% $CO_2$ and 95% air. After separating the cells from the nutrient median, both the number of living cells and the overall number of cells are determined by MTT staining test (MTT=3-(4,5-dimethylthiazol-2-yl)-2,5-diphenyltetrazolium bromide).

Measuring the cell inhibition

Samples of the respective polymer according to the invention are placed in the wells of standard microliter plates and are held there by means of special PTFE inserts which are sterilized beforehand with ethanol. Samples, wells and PTFE inserts are additionally sterilized by irradiation with ultraviolet light for 15 minutes. The cell suspension of known concentration is then added to the polymer samples, and the treated samples are kept at 37° C. in an atmosphere of 95% air and 5% $CO_2$. After eight days have gone by the cells are washed with phosphate buffer solution, suspended in 0.05% by weight trypsin solution and 0.02% by weight EDTA solution at pH 7.4, and counted with the aid of a Coulter counter, The reference sample used is a sample prepared in the same way which is obtained by polymerizing component III of the respective polymer according to the invention. The inhibition of cell proliferation is expressed as a percentage quotient of the number of cells on the reference samples to the number of cells on the polymers according to the invention.

Preparing Samples of the Polymers According to the Invention

Example 1

Under a nitrogen atmosphere, 218.2 g of methyl methacrylate, 12.1 g of methacrylic acid and 14.8 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 16 hours. The resulting product is subsequently precipitated in a fourfold excess of ice-water, then subjected to extraction with water in a Soxhlet for 24 hours and dried in vacuo at 50° C.

Subsequent analysis of the composition by $^1$H-NMR shows:
Methacrylic acid: 14 mol %
Sodium styrenesulfonate: 11 mol %
Methyl methacrylate: 75 mol %

From these values it is found that the ratio of carboxylate groups to sulfonate groups is 1.27.

Example 2

Under a nitrogen atmosphere, 216.3 g of methyl methacrylate, 13.8 g of acrylic acid and 9.9 g of sodium styrenesulfonate are dissolved in 500 ml of dimethyl sulfoxide. The solution is heated to 70° C. with stirring. Then 2 g of azobisisobutyronitrile dissolved in 30 ml of dimethylsulfoxide are added dropwise over the course of 2 minutes. The polymerization is conducted at 70° C. over a period of 16 hours. The resulting product is subsequently precipitated in a fourfold excess of ice-water, then subjected to extraction with water in a Soxhlet for 24 hours and dried in vacuo at 50° C. Subsequent analysis of the composition by $^1$H-NMR shows:
Acrylic acid: 10 mol %
Sodium styrenesulfonate: 9 mol %
Methyl methacrylate: 81 mol %

From these values it is found that the ratio of carboxylate groups to sulfonate groups is 2.14.

Example 3

Under a nitrogen atmosphere, 235 g of styrene, 6.1 g of methacrylic acid and 14.8 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 16 hours. The resulting product is subsequently precipitated in a fourfold excess of ice-water, then subjected to extraction with water in a Soxhlet for 24 hours and dried in vacuo at 50° C. Subsequent analysis of the composition by $^1$H-NMR shows:
Methacrylic acid: 15 mol %
Sodium styrenesulfonate: 7 mol %
Styrene: 78 mol %

From these values it is found that the ratio of carboxylate groups to sulfonate groups is 2.14.

Example 4

Under a nitrogen atmosphere, 227.5 g of styrene, 8.1 g of acrylic acid and 24.7 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 20 hours. The resulting product is subsequently precipitated in a fourfold excess of ice-water, then subjected to extraction with water in a Soxhlet for 24 hours and dried in vacuo at 50° C.

Subsequent analysis of the composition by $^1$H-NMR shows:
Acrylic acid: 11 mol %
Sodium styrenesulfonate: 12 mol %
Styrene: 77 mol %

From these values it is found that the ratio of carboxylate groups to sulfonate groups is 0.9.

Example 5

Under a nitrogen atmosphere, 310.0 g of n-butyl methacrylate, 12.1 g of methacrylic acid and 14.8 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 20 hours. The resulting product is subsequently precipitated in a fourfold excess of ice-water, then subjected to extraction with water in a Soxhlet for 24 hours and dried in vacuo at 50° C.

Subsequent analysis of the composition by $^1$H-NMR shows:
Methacrylic acid: 14 mol %
Sodium styrenesulfonate: 9 mol %
n-butyl methacrylate: 77 mol %

From these values it is found that the ratio of carboxylate groups to sulfonate groups is 1.6.

Example 6

Under a nitrogen atmosphere, 306.7 g of n-butyl methacrylate, 13.8 g of acrylic acid and 9.9 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° over a period of 16 hours. The resulting product is subsequently precipitated in a fourfold excess of ice-water, then subjected to extraction with water in a Soxhlet for 24 hours and dried in vacuo at 50° C.

Subsequent analysis of the composition by $^1$H-NMR shows—
Acrylic acid: 19 mol %
Sodium styrenesulfonate: 8 mol %
n-butyl methacrylate: 82 mol %

From these values it is found that the ratio of carboxylate groups to sulfonate groups is 1.3.

Example 7

Under a nitrogen atmosphere, 220 g of styrene, 15.6 g of acrylic acid and 14.8 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 16 hours. The resulting product is subsequently precipitated in a fourfold excess of ice-water, then subjected to extraction with water in a Soxhlet for 24 hours and dried in vacuo at 50° C. Subsequent analysis of the composition by $^1$H-NMR shows:
Acrylic acid: 19 mol %
Sodium styrenesulfonate: 5 mol %
Styrene: 76 mol %

From these values it is found that the ratio of carboxylate groups to sulfonate groups is 3.8.

Example 8

Under a nitrogen atmosphere, 310.6 g of n-butyl methacrylate, 10.4 g of acrylic acid and 14.8 g of sodium styrenesulfonate are dissolved in 500 ml of dimethyl sulfoxide. The solution is heated to 70° C. with stirring. Then 2.3 g of azobisisobutyronitrile dissolved in 30 ml of dimethylsulfoxide are added dropwise over the course of 2 minutes. The polymerization is conducted at 70° C. over a period of 16 hours. The resulting product is subsequently precipitated in a fourfold excess of ice-water, then subjected to extraction with water in a Soxhlet for 24 hours and dried in vacuo at 50° C.

Subsequent analysis of the composition by $^1$H-NMR shows:
Acrylic acid: 8 mol %
Sodium styrenesulfonate: 11 mol %
n-butyl methacrylate: 81 mol %

From these values it is found that the ratio of carboxylate groups to sulfonate groups is 0.7.

Preparing Membranes from the Polymers According to the Invention

Example 9

A 5% strength dimethyl sulfoxide solution of a polymer according to the invention is prepared. The solution is poured into a Petri dish and the solvent is removed from the sample under reduced pressure at 80° C. The membrane is then cut into sections each of 0.5 cm$^2$ (for the scintillation measurement) or of 2 cm$^2$ (for the ATP measurements) and subjected to extraction with water for 24 hours. Before the following biological investigations the membrane sections are washed three times for three hours in each case in a Michaelis buffer solution (pH=7.33) and are stored at −4° C. until further examination.

The adhesion of the bacterial strains *Staphylococcus epidermidis*, *Streptococcus pyogenes* and *Staphylococcus aureus* was investigated on polymer samples obtained in accordance with Examples 1 to 8. The measurement of the bacterial adhesion to these samples by the scintillation technique and the static determination of the ATP gave bacterial adhesion inhibitions of more than 95%; dynamic determination of the ATP gave bacterial adhesion inhibitions of more than 93%.

Preparing Polymer Coatings by Dipping

Example 10

A 5% strength methyl ethyl ketone solution of a polymer according to the invention is prepared. A 10 cm×8 cm×0.04 cm polyamide film is immersed in this solution for 10 seconds. The film is removed and dried under reduced pressure at 50° C. for 10 hours. The coated film is then cut into sections each of 0.5 cm$^2$ (for the scintillation measurement) or of 2 cm$^2$ (for the ATP measurements) and is subjected to extraction with water for 24 hours. Before the following biological investigations the membrane sections are washed three times for three hours in each case in a Michaelis buffer solution (pH=7.33) and stored at −4° C. until further investigation.

The adhesion of the bacterial strains *Staphylococcus epidermidis*, *Streptococcus pyogenes* and *Staphylococcus aureus* was investigated on polymer samples obtained in accordance with Examples 1 to 8. The measurement of the bacterial adhesion to these samples by the scintillation technique and the static determination of the ATP gave bacterial adhesion inhibitions of more than 99%; dynamic determination of the ATP gave bacterial adhesion inhibitions of more than 96%.

Example 11

A 5% strength acetone solution of a polymer according to the invention is prepared. A 10 cm×8 cm×0.03 cm polyethylene film whose surface has been activated beforehand by treatment for 3 minutes with the 172 nm radiation from an excimer source, is immersed in this solution for 15 seconds. The film is removed and dried under reduced pressure at 50° C. for 10 hours. The coated film is then cut into sections each of 0.5 cm$^2$ (for the scintillation measurement) or of 2 cm$^2$ (for the ATP measurements) and is subjected to extraction with water for 24 hours. Before the following biological investigations the membrane sections are washed three times for three hours in each case in a Michaelis buffer solution (pH=7.33) and stored at −4° C. until further investigation.

The adhesion of the bacterial strains *Staphylococcus epidermidis*, *Streptococcus pyogenes* and *Staphylococcus aureus* was investigated on polymer samples obtained in accordance with Examples 1 to 8. The measurement of the bacterial adhesion to these samples by the scintillation technique and the static determination of the ATP gave bacterial adhesion inhibitions of more than 98%; dynamic determination of the ATP gave bacterial adhesion inhibitions of more than 96%.

Example 12

A 5% strength acetone solution of a polymer according to the invention is prepared. A 10 cm×8 cm×0.04 cm polyether-block-amide film, is immersed in this solution for 10 seconds. The film is removed and dried under reduced pressure at 50° C. for 10 hours. The coated film is then cut into sections each of 0.5 cm$^2$ (for the scintillation measurement) or of 2 cm$^2$ (for the ATP measurements) and is subjected to extraction with water for 24 hours. Before the following biological investigations the membrane sections are washed three times for three hours in each case in a Michaelis buffer solution (pH=7.33) and stored at −4° C. until further investigation.

The adhesion of the bacterial strains *Staphylococcus epidermidis*, *Streptococcus pyogenes* and *Staphylococcus aureus* was investigated on polymer samples obtained in accordance with Examples 1 to 8. The measurement of the bacterial adhesion to these samples by the scintillation technique and the static determination of the ATP gave bacterial adhesion inhibitions of more than 98%, dynamic determination of the ATP gave bacterial adhesion inhibitions of more than 95%.

Conditioning the Samples of Polymers According to the Invention

Example 13

A membrane according to Example 9 and the films coated with the polymers according to the invention, according to Examples 10 to 12, are sterilized by irradiation with ultraviolet light for 15 minutes. The samples pretreated in this way are then held three times for three hours in each case in 0.15 molar sodium chloride solution, and then washed for three hours with distilled water. In the following purification step they are placed three times for three hours in each case in a phosphate buffer solution having the following composition:

| | |
|---|---|
| $CaCl_2 \cdot H_2O$ | 0.132 g/l |
| KCl | 0.2 g/l |
| $KH_2PO_4$ | 0.2 g/l |
| $MgCl_2 \cdot 6H_2O$ | 0.1 g/l |
| NaCl | 8 g/l |
| $Na_2HPO_4$ | 1.15 g/l |

The samples are subsequently irradiated again with ultraviolet light for 15 minutes. These samples are stored for about 16 hours at 37° C. in a DMEM (Dulbecco's Modified Eagles Medium) solution. Finally, the samples are kept at 37° C. under an atmosphere of 5% $CO_2$ and 95% air in a DMEM solution to which antibiotics, L-glutamine and 10% by volume of fetal calf serum have been added.

The polymers according to the invention prepared according to Examples 1, 2 and 5 were either processed to give a membrane (Example 9) or applied to standard polymers (Examples 10 to 12). These samples were subsequently conditioned as in Example 13, and the cell proliferation was determined in accordance with the method described.

For all samples, the inhibition of cell proliferation exceeded 98%.

This application is based upon (1) German patent Application No. 197 00 076.2 filed with the German Patent Office on Jan. 3, 1997, (2) German patent Application No. 197 00 077.0 filed with the German Patent Office on Jan. 3, 1997, (3) German patent Application No. 197 23 132.2 filed with the German Patent Office on Jun. 3, 1997, and (4) German patent Application No. 197 23 131.4 filed with the German Patent Office on Jun. 3, 1997. The entire contents of all four of these German patent Applications are herein incorporated by reference.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A polymer,
   wherein the polymer is water-insoluble, and is bacteriophobic or inhibits cell proliferation,
   wherein the polymer is produced by free-radical copolymerization of component I, component II, and component III,
   wherein component I comprises an aliphatically unsaturated monomer containing a carboxyl group or a salt thereof, or an aliphatically unsaturated monomer containing a substituent that is capable of being converted into a carboxyl group or a salt thereof,
   wherein component II comprises an aliphatically unsaturated monomer containing a sulfonic acid group or a salt thereof, or an aliphatically unsaturated monomer containing a substituent that is capable of being converted into a sulfonic acid group or a salt thereof,
   wherein component III comprises at least one additional aliphatically unsaturated monomer, wherein said at least one additional aliphatically unsaturated monomer excludes acrylonitrile and vinylidene chloride;
   wherein, if component I comprises an aliphatically unsaturated monomer containing the substituent that is capable of being converted into a carboxyl group or a salt thereof, then the substituent is converted into a carboxyl group or a salt thereof after the copolymerization,
   wherein, if component II comprises an aliphatically unsaturated monomer containing the substituent that is capable of being converted into a sulfonic acid group or a salt thereof, then the substituent is converted into a sulfonic acid group or a salt thereof after the copolymerization,
   wherein from 0.5 to 30 mol % of the polymer is derived from component I and component II.

2. The polymer of claim 1,
   wherein the aliphatically unsaturated monomer of component I further contains a sulfonic acid group or a salt thereof, or a substituent that is capable of being converted into a sulfonic acid group or a salt thereof,
   wherein, if the aliphatically unsaturated monomer of component I contains the substituent that is capable of being converted into a sulfonic acid group or a salt thereof, then the substituent is converted into a sulfonic acid group or a salt thereof after the copolymerization.

3. The polymer of claim 1,
   wherein the aliphatically unsaturated monomer of component II further contains a carboxyl group or a salt thereof, or a substituent that is capable of being converted into a carboxyl group or a salt thereof,
   wherein, if the aliphatically unsaturated monomer of component II contains the substituent that is capable of being converted into a carboxyl group or a salt thereof, then the substituent is converted into a carboxyl group or a salt thereof after the copolymerization.

4. The polymer of claim 1, wherein the ratio of the sum of carboxyl groups and carboxylate groups to the sum of sulfonic acid groups and sulfonate groups contained in the polymer is from 0.5 to 10.

5. The polymer of claim 1, wherein the ratio of the sum of carboxyl groups and carboxylate groups to the sum of sulfonic acid groups and sulfonate groups contained in the polymer is from 0.5 to 5.

6. The polymer of claim 1, wherein the ratio of the sum of carboxyl groups and carboxylate groups to the sum of sulfonic acid groups and sulfonate groups contained in the polymer is from 0.4 to 3.

7. The polymer of claim 1, wherein the ratio of the sum of carboxyl groups and carboxylate groups to the sum of sulfonic acid groups and sulfonate groups contained in the polymer is from 0.4 to 2.

8. The polymer of claim 1, wherein the polymer is bacteriophobic and inhibits cell proliferation.

* * * * *